United States Patent [19]

Boublik et al.

[11] Patent Number: 5,328,899
[45] Date of Patent: * Jul. 12, 1994

[54] NPY PEPTIDE ANALOGS

[75] Inventors: Jaroslav H. Boublik, Elwood, Australia; Jean E. F. Rivier, La Jolla; Marvin R. Brown, Del Mar, both of Calif.; Neal A. Scott, Atlanta, Ga.

[73] Assignees: The Salk Institute for Biological Studies, San Diego; The Regents of the University of California, Oakland, both of Calif.

[*] Notice: The portion of the term of this patent subsequent to Jun. 25, 2008 has been disclaimed.

[21] Appl. No.: 882,923

[22] Filed: May 12, 1992

Related U.S. Application Data

[63] Continuation-in-part of Ser. No. 503,198, Mar. 30, 1990, abandoned, which is a continuation-in-part of Ser. No. 219,596, Jul. 15, 1988, Pat. No. 5,026,685.

[51] Int. Cl.$^5$ .................. A61K 37/02; C07K 7/08; C07K 7/10
[52] U.S. Cl. ......................... 514/13; 514/12; 530/324; 530/326
[58] Field of Search ............... 514/12, 13; 530/324, 530/326

[56] References Cited

U.S. PATENT DOCUMENTS

| | | | |
|---|---|---|---|
| 4,728,726 | 3/1988 | Rivier et al. | 514/12 |
| 4,764,504 | 8/1988 | Johnson et al. | 514/12 |
| 5,026,685 | 6/1991 | Boublik et al. | 514/13 |

OTHER PUBLICATIONS

Rioux, F. et al., *Peptides,* 7(1):27–31, 1986.
Boublik, et al., "Synthesis and Hypertensive Activity of Neuropeptide Y Fragments and Analogs with Modified N–or C–Termini..." J. Med. Chem. 32: 597–601, 1989.
Boublik et al., "Neuropeptide $^{18-36}$–An NPY Fragment With Hypotensive Action in Vivo", *Proc. 11th A.P.S.,* Ed. J. Rivier & G. Marshall 1990 pp. 317–318.
Boublik, et al., "Neuropeptide Y and neuropeptide $Y_{1-8-36}$: structural and biological characterization," *Int. J. Peptide Protein Research,* 33:11–15 (1989).
Scott, et al., "Distinction of NPY receptors in vitro and in vivo II. Differential effects of NPY and NPY–(1–8–36)," *J. Med. Chem.,* 35(15):H174–H180 (1990).

Primary Examiner—Lester L. Lee
Attorney, Agent, or Firm—Fitch, Even, Tabin & Flannery

[57] ABSTRACT

Human Neuropeptide Y (NPY) has the formula: H-Tyr-Pro-Ser-Lys-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg -Tyr-NH$_2$. Porcine and rat NPY have the same sequence except for Leu instead of Met in the 17-position. Porcine PYY is homologous having 11 different residues. NPY analogs and N-terminally-shortened fragments, e.g. NPY(18-36), which contain one or more specific D-isomer substitutions for the naturally occurring residues (as well as pharmaceutically acceptable salts thereof), dispersed in a pharmaceutically acceptable liquid or solid carrier, can be administered to mammals, including humans, to substantially lower blood pressure over an extended period of time or to counteract hypertension.

19 Claims, No Drawings

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 36 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Tyr Pro Ser Lys Pro Asp Asn Pro Gly Glu Asp Ala Pro Ala Glu Asp
 1               5                  10                  15

Leu Ala Arg Tyr Tyr Ser Ala Leu Arg His Tyr Ile Asn Leu Ile Thr
                20                  25                  30

Arg Gln Arg Tyr
            35
```

( 2 ) INFORMATION FOR SEQ ID NO:2:

( i ) SEQUENCE CHARACTERISTICS:
        ( A ) LENGTH: 36 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Tyr Pro Ser Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
                20                  25                  30

Arg Gln Arg Tyr
            35
```

( 2 ) INFORMATION FOR SEQ ID NO:3:

( i ) SEQUENCE CHARACTERISTICS:
        ( A ) LENGTH: 36 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

```
Tyr Pro Ala Lys Pro Glu Ala Pro Gly Glu Asp Ala Ser Pro Glu Glu
 1               5                  10                  15

Leu Ser Arg Tyr Tyr Ala Ser Leu Arg His Tyr Leu Asn Leu Val Thr
                20                  25                  30

Arg Gln Arg Tyr
            35
```

( 2 ) INFORMATION FOR SEQ ID NO:4:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
Ala  Arg  Tyr  Tyr  Thr  Gln  Leu  Arg  His  Tyr  Ile  Asn  Leu  Ile  Thr  Arg
 1              5                        10                       15
Gln  Arg  Tyr
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

```
Ala  Arg  Tyr  Tyr  Asp  Ser  Leu  Arg  His  Tyr  Ile  Asn  Thr  Ile  Thr  Arg
 1              5                        10                       15
Gln  Arg  Tyr
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

```
Ala  Arg  Tyr  Tyr  Ser  Ala  Leu  Gln  His  Tyr  Ile  Asn  Leu  Leu  Thr  Arg
 1              5                        10                       15
Pro  Arg  Tyr
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

```
Leu  Ala  Arg  Tyr  Tyr  Ser  Ala  Leu  Arg  Gln  Tyr  Arg  Asn  Leu  Ile  Thr
 1              5                        10                       15
Arg  Gln  Arg  Phe
                20
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
Leu Ala Arg Tyr Tyr Ser Ala Leu Arg His Tyr Ile Asn Leu Ile Thr
1               5                   10                  15

Arg Pro Arg Phe
            20
```

(2) INFORMATION FOR SEQ ID NO:9:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO:9:

```
Ala Lys Tyr Tyr Ser Ala Leu Arg His Phe Val Asn Leu Ile Thr Arg
1               5                   10                  15

Gln Arg Tyr
```

(2) INFORMATION FOR SEQ ID NO:10:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:10:

```
Arg Ile Arg Tyr Tyr Ser Ala Leu Arg His Phe Ile Asn Leu Ile Thr
1               5                   10                  15

Arg Gln Arg Phe
            20
```

(2) INFORMATION FOR SEQ ID NO:11:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:11:

```
Leu Ser Arg Tyr Tyr Ser Ala Leu Arg His Phe Ile Asn Leu Ile Thr
1               5                   10                  15

Arg Gln Arg Tyr
            20
```

(2) INFORMATION FOR SEQ ID NO:12:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:12:

```
Met Ala Arg Tyr Tyr Ser Asp Leu Arg Arg Tyr Ile Asn Leu Ile Thr
1               5                   10                  15

Arg Gln Arg Tyr
            20
```

(2) INFORMATION FOR SEQ ID NO:13:

(i) SEQUENCE CHARACTERISTICS:
        (A) LENGTH: 19 amino acids

-continued

```
    ( B ) TYPE: amino acid
    ( D ) TOPOLOGY: unknown ( i i ) MOLECULE TYPE: peptide ( x i ) SEQUENCE DESCRIPTION: SEQ ID NO:13:

Ala Arg Tyr Tyr Ser Glu Leu Arg His Tyr Ile Ile Leu Ile Thr Arg
 1               5                  10                  15

Gln Arg Tyr
```

( 2 ) INFORMATION FOR SEQ ID NO:14:

```
    ( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:14:

Xaa Xaa Xaa Xaa Xaa Leu Xaa Xaa Xaa Xaa Xaa Xaa Xaa Xaa Arg Xaa
 1               5                  10                  15

Arg Xaa
```

NPY PEPTIDE ANALOGS

This invention was made with Government support under NIH Grants Nos. DK-26741, HL-41910 and HL-43154 awarded by the National Institutes of Health. The Government has certain rights in this invention.

This application is a continuation-in-part of our application Ser. No. 503,198 filed Mar. 30, 1990 and now abandoned, which is a continuation-in-part of our application Ser. No. 219,596, filed Jul. 15, 1988, now U.S. Pat. No. 5,026,685, issued Jun. 25, 1991.

This invention is generally directed to the field of Neuropeptide Y(NPY) and to methods for pharmaceutical treatment of mammals using analogs of such a peptide. More specifically, the invention relates to NPY analogs, to pharmaceutical compositions containing such peptide analogs and to methods of treatment of mammals using such peptide analogs to lower blood pressure.

BACKGROUND OF THE INVENTION

Experimental and clinical observations have supported the concept that neuropeptides play central roles in neurotransmission as well as the regulation of secretory functions of adenohypophysial, pancreatic, adrenalcortical and gut cells. Among the thirty or so neuropeptides that have been implicated in neuronal function in the mammalian central nervous system, several have also been suggested to function as neurotransmitters or neuromodulators primarily in afferent neurons.

NPY is a 36-residue, amidated peptide hormone which was first isolated from porcine brain and characterized. NPY is anatomically co-distributed and co-released with norepinephrine in and from sympathetic postganglionic neurons. Stimulation of the sympathetic nervous system under physiologic circumstances, e.g. exercise, cold exposure, surgical stress, etc., promotes an elevation of plasma concentrations of NPY. NPY is believed to participate along with norepinephrine in the regulation of vascular smooth muscle tone and maintenance of blood pressure. In addition to the post-synaptic action to increase vascular smooth muscle tone, NPY may also act presynaptically to inhibit both its own release and that of norepinephrine. This mechanism is similar to the presynaptic actions of norepinephrine that, acting through certain receptors, facilitates a local feedback regulation of the neurohumoral regulation of blood pressure. Over the past 30 years, knowledge of norepinephrine's role in regulation of blood pressure has resulted in increasing our understanding of cardiovascular regulation and the successful development of a variety of pharmacotherapeutic substances used clinically to treat disorders of cardiovascular function. These compounds are, in general, structural analogs of norepinephrine and serve as either agonists or antagonists of norepinephrine to treat hypotension or hypertension, respectively. These drugs, however useful, have not solved the problems of management of a variety of cardiovascular disorders.

An additional action of NPY is to decrease cardiac contractility (inotropy). This is an extremely important action of NPY, because it is known that, under many circumstances in which inotropy is decreased, diseases of life-threatening importance, e.g. congestive heart failure and cardiogenic shock, are associated with probable increased release of NPY into the blood. Prevention of NPY release, using a presynaptic NPY agonist, or NPY's action, using a postsynaptic NPY antagonist, may be beneficial in these disease states.

NPY has also been reported to produce coronary artery vasoconstriction and thereby may decrease myocardial blood flow resulting in myocardial ischemia. Such a circumstance can result in angina pectoris or, under more severe circumstances, may result in myocardial infarction and death. In recent years, several classes of drugs have proven effective in dilating coronary arteries to prevent such events. The use of analogs of NPY are expected to prove useful in treatment of such problems.

Porcine NPY has the formula (SEQ ID NO:1): Tyr-Pro-Ser-Lys-Pro-Asp-Asn-Pro-Gly-Glu-Asp-Ala-Pro-Ala-Glu-Asp-Leu-Ala-Arg-Tyr-Tyr-Ser-Ala-Leu-Arg-His-Tyr-Ile-Asn-Leu-Ile-Thr-Arg-Gln-Arg -Tyr, wherein the C-terminus is amidated. The formula of Human NPY has been deduced from clones obtained from total RNA by preparing cDNA and then employing DNA sequencing technologies and is accepted to be (SEQ ID NO:2): Tyr-Pro-Ser-Lys-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg -Tyr, wherein the C-terminus is amidated.

Peptide YY (porcine) (PYY) has the formula (SEQ ID NO:3): Tyr-Pro-Ala-Lys-Pro-Glu-Ala-Pro-Gly-Glu-Asp-Ala-Ser-Pro-Glu-Glu-Leu-Ser-Arg-Tyr-Tyr-Ala-Ser-Leu-Arg-His-Tyr-Leu-Asn-Leu-Val -Thr-Arg-Gln-Arg-Tyr, wherein the C-terminus is amidated.

SUMMARY OF THE INVENTION

NPY has a wide range of biological actions including cardiovascular effects such as increasing mean arterial pressure (MAP) when injected into conscious rats. Administration of NPY analogs which are shortened at the N-terminus and which may have a D-isomer substitution at at least one position in the chain substantially decrease the MAP. The following peptides, hereinafter termed NPY analogs, are preferred, which peptides have one of the following formulae:

(a) H-Ala-Arg-Tyr-$Xaa_{21}$-$Xaa_{22}$-Ala-Leu-Arg-His-$Xaa_{27}$-Ile-$Xaa_{29}$-$Xaa_{30}$-$Xaa_{31}$-$Xaa_{32}$-Arg-$Xaa_{34}$-$Xaa_{35}$-$Xaa_{36}$-$NH_2$ wherein $Xaa_{21}$ is Tyr or D-Tyr; $Xaa_{22}$ is Ser or D-Ser; $Xaa_{27}$ is Tyr or D-Tyr; $Xaa_{29}$ is Asn or D-Asn; $Xaa_{30}$ is Leu or D-Leu; $Xaa_{31}$ is Ile or D-Ile; $Xaa_{32}$ is Thr or D-Thr; $Xaa_{34}$ is Gln or D-Gln; $Xaa_{35}$ is Arg or D-Arg; and $Xaa_{36}$ is Tyr or D-Tyr; and wherein at least one D-isomer is present; and (b) H-Ser-Arg-Tyr-$Xaa_{21}$-$Xaa_{22}$-Ser-Leu-Arg-His-$Xaa_{27}$-Leu-$Xaa_{29}$-$Xaa_{30}$-$Xaa_{31}$-$Xaa_{32}$-Arg-$Xaa_{34}$-$Xaa_{35}$-$Xaa_{36}$-$NH_2$, wherein $Xaa_{21}$ is Tyr or D-Tyr; $Xaa_{22}$ is Ala or D-Ala; $Xaa_{27}$ is Tyr or D-Tyr; $Xaa_{29}$ is Asn or D-Asn; $Xaa_{30}$ is Leu or D-Leu; $Xaa_{31}$ is Val or D-Val; $Xaa_{32}$ is Thr or D-Thr; $Xaa_{34}$ is Gln or D-Gln; $Xaa_{35}$ is Arg or D-Arg; and $Xaa_{36}$ is Tyr or D-Tyr; and wherein at least one D-isomer is present.

Such analogs of NPY, which preferably include one or two D-isomers, have the following applications: potent post-synaptic treatment of hypertension and cardiogenic shock, the treatment of acute cardiovascular circulatory failure, and the elevation of intracellular calcium.

These synthetic peptide NPY analogs substantially lower blood pressure for an extended time period. Pharmaceutical compositions in accordance with the invention include NPY analogs, or nontoxic addition salts thereof, dispersed in a pharmaceutically acceptable liquid or solid carrier. Such peptides or pharmaceutically acceptable addition salts thereof may be administered to mammals in accordance with the invention for lowering blood pressure or other regulation as described above.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the N-terminus appears to the left and the C-terminus to the right. Where the amino acid residue has isomeric forms, it is the L-form of the amino acid that is represented herein unless otherwise expressly indicated. By Nva is meant norvaline, and by Nle is meant norleucine.

Very broadly, NPY analogs are provided having the following formula (SEQ ID NO:14), with the Xaa groups being defined using subscripts beginning with $Xaa_{19}$ from left to right by position: Xaa-Xaa-Xaa-Xaa-Xaa-Leu-Xaa-Xaa-Xaa-Xaa-Xaa-Xaa-Xaa-Arg-Xaa-Arg-Xaa wherein X-Q is present at the N-terminus; X is H or $C^{\alpha}Me$ or $N^{\alpha}Me$ or desamino or an acyl group having 7 carbon atoms or less; Q is $Xaa_{17}$-$Xaa_{18}$, $Xaa_{18}$ or desQ; $Xaa_{17}$ is Met, Arg, Nle, Nva, Leu, Ala or D-Ala; $Xaa_{18}$ is Ala, Ser, Ile, D-Ala, D-Ser or D-Ile; $Xaa_{19}$ is Arg, Lys, Gln or des $Xaa_{19}$; $Xaa_{20}$ is Tyr, Phe or des $Xaa_{20}$; $Xaa_{21}$ is Tyr, Glu, His, Ala or des $Xaa_{21}$; $Xaa_{22}$ is Ser, Ala, Thr, Asn or Asp; $Xaa_{23}$ is Ala, Asp, Glu, Gln, Asn or Ser; $Xaa_{25}$ is Arg or Gln; $Xaa_{26}$ is His, Arg or Gln; $Xaa_{27}$ is Phe or Tyr; $Xaa_{28}$ is Ile, Leu, Val or Arg; $Xaa_{29}$ is Asn or Ile; $Xaa_{30}$ is Leu, Met, Thr or Val; $Xaa_{31}$ is Ile, Val or Leu; $Xaa_{32}$ is Thr or Phe; $Xaa_{34}$ is Gln, Pro or His; $Xaa_{36}$ is Phe or Tyr; and the C-terminus may be amidated; provided however that one or more of the residues in positions 21-23 and/or positions 26-36 is preferably substituted by the D-isomer thereof. When X is not H, $C^{\alpha}Me$ $N^{\alpha}Me$, or desamino, X is preferably acetyl (Ac), acrylyl (Acr), formyl (For) or benzoyl (Bz); however, X is most preferably H.

Certain preferred NPY analogs have the formula: H-$Xaa_{18}$-Arg-Tyr-Tyr-$Xaa_{22}$-$Xaa_{23}$-Leu-Arg-His-$Xaa_{27}$-$Xaa_{28}$-Asn-Leu-$Xaa_{31}$-Thr-Arg-Gln-Arg-$Xaa_{36}$-$NH_2$, wherein $Xaa_{18}$ is Ala or Ser; $Xaa_{22}$ is Ser or Ala; $Xaa_{23}$ is Ala or Ser; $Xaa_{27}$ is Phe or Tyr; $Xaa_{28}$ is Ile or Leu; $Xaa_{31}$ is Ile or Val; and $Xaa_{36}$ is Phe or Tyr; provided that at least one of the residues in positions 21-23 and 26-36 is a D-isomer of the residue indicated.

Other preferred NPY analogs have the formula: H-$Xaa_{17}$-$Xaa_{18}$ -Arg-Tyr-Tyr-Ser-Ala-Leu-Arg-His-Tyr-Ile -Asn-Leu-Ile-Thr-Arg-Gln-Arg-Tyr-$NH_2$, wherein $Xaa_{17}$ is Arg, Leu or des $Xaa_{17}$; $Xaa_{18}$ is Ser or Ala or Ile; and wherein at least one of the residues in positions 21-23 and 26-36 is a D-isomer of the residue indicated.

Still other preferred NPY analogs have the formula: H-A1 a-Arg-Tyr-$Xaa_{21}$-$Xaa_{22}$-Ala-Leu-Arg-His-$Xaa_{27}$-Ile-$Xaa_{29}$-$Xaa_{30}$-$Xaa_{31}$-$Xaa_{32}$-Arg-$Xaa_{34}$-$Xaa_{35}$-$Xaa_{36}$-$NH_2$, wherein $Xaa_{21}$ is Tyr or D-Tyr, $Xaa_{22}$ is Ser or D-Ser, $Xaa_{27}$ is Tyr or D-Tyr, $Xaa_{29}$ is Asn or D-Asn, $Xaa_{30}$ is Leu or D-Leu, $Xaa_{31}$ is Ile or D-Ile, $Xaa_{31}$ is Thr or D-Thr, $Xaa_{34}$ is Gln or D-Gln, $Xaa_{35}$ is Arg or D-Arg, and $Xaa_{36}$ is Tyr or D-Tyr, wherein at least one D-isomer is present.

Another preferred NPY analog group has the formula: H-Ser-Arg-Tyr-$Xaa_{21}$-$Haa_{22}$-Ser-Leu-Arg-His-$Xaa_{27}$-Leu-$Xaa_{29}$-$Xaa_{30}$-$Xaa_{31}$-$Xaa_{32}$-Arg-$Xaa_{34}$-$Xaa_{35}$ -$Xaa_{36}$-$NH_2$, where in $Xaa_{21}$ is Tyr or D-Tyr, $Xaa_{22}$ is Ala or D-Ala, $Xaa_{27}$ is Tyr or D-Tyr, $Xaa_{29}$ is Asn or D-Asn, $Xaa_{30}$ is Leu or D-Leu, $Xaa_{31}$ is Val or D-Val, $Xaa_{32}$ is Thr or D-Thr, $Xaa_{34}$ is Gln or D-Gln, $Xaa_{35}$ is Arg or D-Arg, and $Xaa_{36}$ is Tyr or D-Tyr; and N-terminally shortened fragments thereof, wherein either 1 or 2 D-isomers are present.

Still other preferred NPY analogs have the formula: H-$Xaa_{18}$-Arg-Tyr-$Xaa_{21}$-$Xaa_{22}$-$Xaa_{23}$-Leu-Arg-His-$Xaa_{27}$-$Xaa_{28}$-Asn-Leu-$Xaa_{31}$-Thr-Arg-Gln-$Xaa_{35}$-Tyr-$NH_2$, wherein $Xaa_{18}$ is Ala or Ser; $Xaa_{21}$ is Tyr or D-Tyr, $Xaa_{22}$ is Ser or Ala, $Xaa_{23}$ is Ala or Ser, $Xaa_{27}$ is Tyr or D-Tyr, $Xaa_{28}$ is Ile or Leu, $Xaa_{31}$ is Ile or Val, and $Xaa_{35}$ is Arg or D-Arg; wherein one D-isomer is present.

There is also provided a method for lowering the blood pressure of a mammal, which method comprises administering an effective amount of a synthetic peptide, or a nontoxic salt thereof, having the formula: H-Ala-Arg-Tyr-$Xaa_{21}$ -$Xaa_{22}$-Ala-Leu-Arg-His-$Xaa_{27}$-Ile-$Xaa_{29}$-$Xaa_{30}$-$Xaa_{31}$- $Xaa_{32}$-Arg-$Xaa_{34}$-$Xaa_{35}$-$Xaa_{36}$-$NH_2$, wherein $Xaa_{21}$ is Tyr or D-Tyr, $Xaa_{22}$ is Ser or D-Ser, $Xaa_{27}$ is Tyr or D-Tyr, $Xaa_{29}$ is Asn or D-Asn, $Xaa_{30}$ is Leu or D-Leu, $Xaa_{31}$ is Ile or D-Ile, $Xaa_{32}$ is Thr or D-Thr, $Xaa_{34}$ is Gln or D-Gln, $Xaa_{35}$ is Arg or D-Arg, and $Xaa_{36}$ is Tyr or D-Tyr; provided that at least one D-isomer is present.

In addition, there is also provided a method for lowering the blood pressure of a mammal, which method comprises administering an effective amount of a synthetic peptide, or a nontoxic salt thereof, having the formula: H-$Xaa_{18}$-Arg-Tyr-$Xaa_{21}$-$Xaa_{22}$-$Xaa_{23}$-Leu-Arg-His-$Xaa_{27}$-$Xaa_{28}$-$Xaa_{29}$-$Xaa_{30}$-$Xaa_{31}$-$Xaa_{32}$-Arg-$Xaa_{34}$-$Xaa_{35}$-$Xaa_{36}$-$NH_2$, wherein $Xaa_{18}$ is Ala or Ser; $Xaa_{21}$ is Tyr or D-Tyr; $Xaa_{22}$ is Ser, D-Ser, Ala or D-Ala; $Xaa_{23}$ is Ala or Ser; $Xaa_{27}$ is Tyr or D-Tyr; $Xaa_{28}$ is Ile or Leu; $Xaa_{29}$ is Asn or D-Asn; $Xaa_{30}$ is Leu or D-Leu; $Xaa_{31}$ is Ile, D-Ile, Val or D-Val; $Xaa_{32}$ is Thr or D-Thr; $Xaa_{34}$ is Gln or D-Gln; $Xaa_{35}$ is Arg or D-Arg; and $Xaa_{36}$ is Tyr or D-Tyr; provided that at least one D-isomer is present.

The peptides can be synthesized by any suitable method, such as by exclusively solid-phase techniques, by partial solid-phase techniques, by fragment condensation or by classical solution addition. Synthetic NPY analogs may also be entirely or partially synthesized by recently developed recombinant DNA techniques, which may likely be used for large-scale production.

For example, the techniques of exclusively solid-phase synthesis are set forth in the textbook "Solid-Phase Peptide Synthesis" Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Synthesis by the use of recombinant DNA techniques, for purposes of this application, should be understood to include the suitable employment of a structural gene coding for all or an appropriate section of the NPY analog to transform a microorganism, using an expression vector including a promoter and operator together with such structural gene, and causing such transformed microorganism to express the peptide or such a synthetic peptide fragment. A non-human animal may also be used to produce the peptide by gene-farming using such a structural gene in the microinjection of embryos as described in U.S. Pat. No. 4,870,009 issued Sep. 26, 1989.

Common to coupling-type chemical syntheses of peptides is the protection of the labile side chain groups of the various amino acid moieties with suitable protecting groups which prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

In preparing the peptides of the present invention, intermediates may be created such as those having the formula (II): $X_1$-$Xaa_{17}(X^7)$-$Xaa_{18}(X^3)$-$Xaa_{19}(X^4$ or $X^6$ or $X^7)$-$Xaa_{20}(X^2)$-$Xaa_{21}(X^2$ or $X^5$ or $Xs)$-$Xaa_{22}(X^3$ or $X^5$ or $X_6)$-$Xaa_{23}(X^3$ or $X^5$ or $X^6)$-$Leu$-$Xaa_{25}(X^6$ or $X^7)$-$Xaa_{26}(X^6$ or $X^7$ or $X^8)$ -$Xaa_{27}(X^2)$ -$Xaa_{28}(X^7)$-$Xaa_{29}(X^6)$-$Xaa_{30}(X^3)$-$Xaa_{31}$-$Xaa_{32}(X^3)$-$Arg$ $(X^7)$-$Xaa_{34}(X^6$ or $X^8)$-$Arg(X^7)$-$Xaa_{36}(X_2)$-$X^9$ wherein the R-groups are as hereinbefore defined.

$X^1$ is either hydrogen or an alpha-amino protecting group and when X in the desired peptide is a particular acyl group, that group can be used as the protecting group. The alpha-amino protecting groups contemplated by $X^1$ are those known to be useful in the art in the step-wise synthesis of polypeptides. Among the classes of alpha-amino protecting groups which may be urethane X used as $X^1$ are: (1) aromatic urethane-type protecting groups, such as fluorenylmethyloxycarbonyl (FMOC), benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (2) aliphatic urethan protecting groups, such as t-butyloxycarbonyl(BOC), diisopropylmethoxycarbonyl, isopropyloxycarbonyl, ethoxycarbonyl, allyloxycarbonyl; and (3) cycloalkyl urethan-type protecting groups, such as and cyclopentyloxycarbonyl, adamantyloxycarbonyl,and cyclohexyloxycarbonyl. The preferred alpha-amino protecting group is BOC.

$X^2$ is a protecting group for the phenolic hydroxyl group of Tyr, selected from the group consisting of tetrahydropyranyl, tert-butyl, trityl, benzyl, Z, 4-bromobenzyloxycarbonyl, 2-bromobenzyloxycarbonyl (2BrZ) and 2,6-dichlorobenzyl(DCB). 2BrZ is preferred.

$X^3$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl(DCB). The most preferred protecting group is Bzl. $X^3$ can be hydrogen, which means there is no protecting group on the hydroxyl group.

$X^4$ is hydrogen or a protecting group for the side chain amino group of Lys, such as 2-chlorobenzyloxycarbonyl(2-Cl-Z), Tos, CBZ, t-amyloxycarbonyl and BOC.

$X^5$ is hydrogen or an ester-forming protecting group for the side chain carboxyl group of Asp and Glu, preferably selected from the class consisting of benzyl, 2,6-dichlorobenzyl, β or γ-cyclohexyl (CyHx), methyl, ethyl and t-butyl ester. CyHx is most preferred.

$X^6$ is hydrogen or a protecting group for the amino group of Asn and Gln such as xanthyl(Xan). It is preferably left unprotected and coupled in the presence of 2 eg. of HOBt.

$X^7$ is a protecting group for the guanidino group of Arg preferably selected from the class consisting of nitro, p-toluenesulfonyl(Tos), Z, adamantyloxycarbonyl and BOC, or is hydrogen. Tos is most preferred.

$X^8$ is hydrogen or a protecting group for the imidazole nitrogen of His, such as Tos or 2,4-dinitrophenyl (DNP).

Although the side chain methylthio group of Met can be protected by oxygen or the like, preferably Met is left unprotected.

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ may be $NH_2$, or an ester or amide anchoring bond used in solid phase synthesis for linking to a solid resin support, represented by the formula:

—O—$CH_2$-polystyrene resin support,
—O—$CH_2$-benzyl-polyamide resin support,
—NH-benzhydrylamine (BHA) resin support, and
—NH-paramethylbenzhydrylamine (MBHA) resin support. The polyamide polymer is commercially available and is discussed in detail in Bioorganic Chemistry, 8, 351–370 (1979) where a preferred version of it is discussed in FIG. 6 therein. Use of BHA or MBHA resin is preferred, and cleavage directly gives the NPY analog amide.

When X is acetyl(Ac), for example, in the final formula, it may be possible to employ it as the $X^1$ protecting group for the alpha-amino group of, for example, Ala by adding it to such amino acid before the coupling of this last amino acid to the peptide chain. However, a reaction is preferably carried out with the peptide on the resin (after deblocking the alpha-amino group while the side-chain groups remain protected), e.g. by reacting with acetic acid in the presence of dicyclohexyl carbodiimide(DCC) or preferably with acetic anhydride or by another suitable reaction as known in the art. Other examples of X include acrylyl and benzoyl which can be similarly incorporated.

In the Formula (II) for the intermediate, at least one of $X^1$, $X^2$, $X^3$, $X^4$, $X^5$, $X^6$, $X^7$, $X^8$ and $X^9$ is a protecting group or an anchoring bond. Thus, there are also provided methods for manufacturing an NPY peptide analog of interest by (a) first forming a peptide of Formula (II) wherein: X, $X^1$, $X^2$, $X^3$, $X^4$, $X^5$, $X^6$, $X^7$ and $X^8$ are each either hydrogen or a protective group and $X^9$ is either a protective group or an anchoring bond to resin support or $NH_2$, with at least one X-group being either a protecting group or an anchoring bond; (b) splitting off the protective group or groups or anchoring bond from said peptide of Formula (II); and (c) if desired, converting the resulting peptide of interest into a nontoxic salt thereof.

In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

When the peptides are not prepared using recombinant DNA technology, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for NPY analogs can, for example, be prepared by attaching alpha-amino- and side-chain-protected Tyr to a BHA resin.

Tyr protected by BOC and DCB is coupled to the BHA resin using methylene chloride or dimethylformamide (DMF) as solvent with a suitable coupling reagent. The selection of an appropriate coupling reagent is within the skill of the art. Particularly suitable as a coupling reagent is N,N'-dicyclohexyl carbodiimide (DCC). The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Following the coupling of BOC-Tyr(DCB) to the resin support, the alpha-amino protecting group is removed, as by using trifluoroacetic acid(TFA) in methylene chloride, TFA alone or with HCl in dioxane. Preferably 50 % TFA in methylene chloride is used with 0–5 % 1,2 ethanedithiol. The deprotection is carried out at a temperature between about 0° C. and room temperature. Other standard cleaving reagents and conditions for removal of specific alpha-amino protecting groups may be used as described in Schroder & Lubke, "The Peptides" 1 , pp 72–75 (Academic Press 1965).

After removal of the alpha-amino protecting group, the remaining alpha-amino- and side-chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. Each protected amino acid or amino acid sequence is introduced into the solid phase reactor in about a two to fourfold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis can be monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers,* 1978, 17, pp.1927–1938.

After the desired amino acid sequence has been completed, the intermediate peptide is removed from the resin support by treatment with a reagent, such as liquid hydrogen fluoride, which not only cleaves the peptide from the resin but also cleaves the alpha-amino protecting group $X^1$ and all remaining side chain protecting groups $X^2$, $X^3$, $X^4$, $X^5$, $X^6$, $X^7$ and $X^8$ to obtain the peptide.

The following Examples set forth preferred methods for synthesizing NPY analogs by the solid-phase technique and generally is in accordance with the procedure set forth in U.S. Pat. No. 4,415,558 to Vale, et al, issued Nov. 15, 1983, the disclosure of which is incorporated herein by reference.

EXAMPLE I

The synthesis of pNPY(17–36), see SEQ ID NO:1, is conducted in a stepwise manner on a methylbenzhydrylamine hydrochloride resin, such as available from Bachem, Inc., having a substitution range of about 0.1 to 0.5 mmoles/gm. resin. The synthesis is performed on an automatic Beckman 990B peptide synthesizer under an $N_2$ atmosphere. Coupling of BOC-Tyr(2BrZ) results in the substitution of about 0.35 mmol. Tyr per gram of resin. The program used is generally that reported in Marki et al., *J. Am. Chem. Soc.*, 103, 3178–3185 (1981).

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn and Gln, and for example, BOC-Asn(ONp) is coupled overnight using one equivalent of HOBt in a 50% mixture of DMF and methylene chloride. Although the amido group of Asn or Gln may be protected by Xan when DCCI coupling is used instead of the active ester method, BOC-Asn or BOC-Gln is preferably used in the presence of 2 eq. N-hydroxybenzotriazole per equivalent of BOC-AA. Tos is used to protect the guanidino group of Arg and the imidazole group of His, and the side chain carboxyl group of Asp and Glu is protected by OBzl. At the end of the synthesis, the following composition is obtained: $X_1$-Leu-Ala-Arg ($X^7$) -Tyr ($X^2$) -Tyr ($X^2$) -Ser ($X^3$) -Ala-Leu-Arg ($X^2$) -His($X^8$) -Tyr($X^2$)-Ile-Asn-Leu-Ile-Thr($X^3$)-Arg($X^7$) -Gln-Arg ($X^7$)-Tyr($X^2$)-MBHA resin; wherein $X_1$ is BOC, $X_2$ is 2BrZ, $X_3$ is Bzl, $X_7$ is Tos and $X_8$ is DNP. Xan may have been partially or totally removed by TFA treatment used to deblock the alpha-amino protecting group.

In order to cleave and substantially deprotect the resulting protected peptide-resin, it is treated with 1.5 ml. anisole, and 30 ml. hydrogen fluoride(HF) per gram of peptide-resin, first at −20° C. for 20 min. and then at 0° C. for 40 minutes. After elimination of the HF under high vacuum, the resin-peptide is washed with dry diethyl ether, and the peptides are then extracted with water and separated from the resin by filtration.

The cleaved peptide is then purified by reverse-phase HPLC and then rechromatographed for final purification using preparative HPLC as described in Rivier et al., Peptides: Structure and Biological Function (1979)

pp. 125–128. The chromatographic fractions are carefully monitored by HPLC, and only the fractions showing substantial purity are pooled.

EXAMPLE II

The peptide hNPY(17–36), see SEQ ID NO:2, synthesized using the method as described in Example I.

EXAMPLE III

The peptides NPY(18–36) and [Phe$^{27}$]-NPY(18–36) are synthesized using the method as described in Example I.

EXAMPLE IV

The peptide [Ac-D-Ala$^{17}$]-NPY(17–36) having the formula: Ac-D-Ala-Ala-Arg-Tyr-Tyr-Ser-Ala-Leu-Arg-His-Tyr-Ile-Asn-Leu-Ile-Thr-Arg-Gln-Arg-Tyr-NH$_2$ is synthesized using the general method as described in Example I, and then reacting with acetic acid in the presence of DCC, or reacting with acetic anhydride, after deblocking the alpha-amino group on the final D-Ala residue.

EXAMPLE V

The peptide NPY(19–36) is synthesized using the method as described in Example I.

EXAMPLE VI

The peptide [Nle$^{17}$]-NPY(17–36) is synthesized using the method as described in Example I.

EXAMPLE VII

The peptide [D-Ser$^{18}$]-NPY(18–36) having the formula: H-D-Ser-Arg-Tyr-Tyr-Ser-Ala-Leu-Arg-His-Tyr-Ile-Asn-Leu-Ile-Thr-Arg-Gln-Arg-Tyr-NH$_2$ is synthesized using the method as described in Example I.

EXAMPLE VIII

The peptide [Ala$^{17}$, His$^{21}$]-NPY(17–36) is synthesized using the method as described in Example I.

EXAMPLE IX

The peptide [D-Ile$^{18}$]-NPY(18–36) having the formula: D-Ile-Arg-Tyr-Tyr-Ser-Ala-Leu-Arg-His-Tyr-Ile-Asn-Leu-Ile-Thr-Arg-Gln-Arg-Tyr-NH$_2$ is synthesized using the method as described in Example I.

EXAMPLE X

The peptide [Ac-Arg$_{17}$]-NPY(17–36) is synthesized using the general method as described in Example I, and then reacting with acetic acid in the presence of DCC, or reacting with acetic anhydride, after deblocking the alpha-amino group on the final residue.

EXAMPLE XI

The peptide [Gln$^{19}$]-NPY(19–36) is synthesized using the method as described in Example I.

EXAMPLE XII

The peptide [Phe$^{20}$]-NPY(18–36) is synthesized using the method as described in Example I.

EXAMPLE XIII

The peptide [C$^\alpha$MeLeu$_{17}$]-pNPY(17–36) is synthesized using the method as described in Example I.

EXAMPLE XIV

The peptide [N$^\alpha$MeLeu$^{17}$]-pNPY(17–36) is synthesized using the method as described in Example I.

EXAMPLE XV

The peptide [desaminoAla$^{18}$]-NPY (18–36) is synthesized using the method as described in Example I.

EXAMPLE XVI

The peptide [For-Ala$^{18}$, Glu$_{23}$, Arg$_{26}$]-NPY(18–36) is synthesized using the general method as described in Example I to create the peptide chain, and the BOC protecting group on the final Ala residue is removed. The peptide-resin is then treated with 98% formic acid at 5°–15° C. and acetic anhydride is added dropwise, and the reaction mixture is stirred for 1 hour. After completion of the reaction, cleavage from the resin and of the protecting groups takes place as set forth in Example I.

EXAMPLE XVII

The peptide [Nva$^{17}$, Ala$^{21}$, Leu$^{28}$]-NPY(17–36) is synthesized using the method as described in Example I.

EXAMPLE XVIII

The peptide [Thr$^{22}$, Gln$^{23}$]-NPY(18–36) having the formula (SEQ ID NO:4): Ala-Arg-Tyr-Tyr-Thr-Gln-Leu-Arg-His-Tyr-Ile-Asn-Leu-Ile-Thr-Arg-Gln-Arg-Tyr, wherein the C-terminus is amidated, is synthesized using the method as described in Example I.

EXAMPLE XIX

The peptide [desamino Leu$^{17}$, Asn$^{23}$, Val$_{30}$]-NPY(1–7–36) is synthesized using the general method as described in Example I.

EXAMPLE XX

The peptide [Asp$^{22}$, Ser$_{23}$, Thr$^{30}$]-NPY(18–36) having the formula (SEQ ID NO:5): Ala-Arg-Tyr-Tyr-Asp-Ser-Leu-Arg-His-Tyr-Ile-Asn-Thr-Ile-Thr-Arg-Gln-Arg-TYr, wherein the C-terminus is amidated, is synthesized using the method as described in Example I.

EXAMPLE XXI

The peptide [Gln$^{25}$, Leu$^{31}$, Pro$^{34}$]-NPY(18–36) having the formula (SEQ ID NO: 6): Ala-Arg-Tyr-Tyr-Ser-Ala-Leu-Gln-His-Tyr-Ile-Asn-Leu-Leu-Thr-Arg-Pro-Arg-Tyr, wherein the C-terminus is amidated, is synthesized using the method as described in Example I.

EXAMPLE XXII

The peptide [Gln$^{26}$, Arg$^{28}$,Phe$^{36}$]-NPY (17–36) having the formula (SEQ ID NO:7): Leu-Ala-Arg-Tyr-Tyr-Ser-Ala-Leu-Arg-Gln-Tyr-Arg-Asn-Leu-Ile-Thr-Arg-Gln-Arg-Phe, wherein the C-terminus is amidated, is synthesized using the method as described in Example I.

EXAMPLE XXIII

The peptide [Phe$_{36}$]-pPYY(19–36) is synthesized using the method as described in Example I.

EXAMPLE XXIV

The peptide pPYY(18–36) is synthesized using the method as described in Example I.

EXAMPLE XXV

The peptide [Ac-Ser$^{18}$,Phe$^{27}$]-pPYY(18–36) having is synthesized using the general method as described in Example I, and then reacting with acetic anhydride, after deblocking the alpha-amino group on the final Ser residue.

EXAMPLE XXVI

The peptide [Nle$^{17}$,Asn$^{22}$,Phe$^{27}$]-NPY (17–36) is synthesized using the method as described in Example I.

EXAMPLE XXVII

The peptide [D-Ala$^{18}$, Glu$^{21}$, His$^{34}$]-NPY(18–36) having the formula: H-D-Ala-Arg-Tyr-Glu-Ser-Ala-Leu-Arg-His-Tyr-Ile-Asn-Leu-Ile-Thr-Arg-His-Arg-Tyr-NH$_2$ is synthesized using the method as described in Example I.

EXAMPLE XXVIII

The peptide [Bz-Leu$^7$, Pro$_{34}$,Phe$_{36}$]-pNPY(17–36) having the formula (SEQ ID NO:8): Leu-Ala-Arg-Tyr-Tyr-Ser-Ala-Leu-Arg-His-Tyr-Ile-Asn-Leu-Ile-Thr-Arg-Pro-Arg-Phe, wherein the N-terminal is acylated with benzoyl and the C-terminus is admidated, is synthesized using the general method as described in Example I, and then reacting with benzoic acid in the presence of DCC after removing the BOC group on the final Leu residue.

EXAMPLE XXIX

The peptide [Lys$^{19}$, Phe$^{27}$, Val$^{28}$]-NPY(18–36) having the formula (SEQ ID NO:9): Ala-Lys-Tyr-Tyr-Ser-Ala-Leu-Arg-His-Phe-Val-Asn-Leu-Ile-Thr-Arg-Gln-Arg-Tyr, wherein the C-terminus is amidated, is synthesized using the method as described in Example I.

EXAMPLE XXX

The peptide [D-Ala$^{17}$, Val$^M$, Phe$_{32}$]-NPY(17–36) having the formula: D-Ala-Ala-Arg-Tyr-Tyr-Ser-Ala-Leu-Arg-His-Tyr-Val-Asn-Leu-Ile-Phe-Arg-Gln-Arg-Tyr-NH$_2$ is synthesized using the general method as described in Example I, and then reacting with acetic acid in the presence of DCC, or reacting with acetic anhydride, after deblocking the alpha-amino group on the final D-Ala residue.

EXAMPLE XXXI

The peptide [C$^\alpha$MeSer$^{18}$, Met$^{30}$, Phe$^{36}$]-Npy(18–36) is synthesized using the method as described in Example I.

EXAMPLE XXXII

The peptide [Arg$^{17}$, Ile$^{18}$, Phe$_{27,36}$]-Npy(17–36) having the formula (SEQ ID NO:10): Arg-Ile-Arg-Tyr-Tyr-Ser-Ala-Leu-Arg-His-Phe-Ile-Asn-Leu-Ile-Thr-Arg-Gln-Arg-Phe, wherein the C-terminus is amidated, is synthesized using the method as described in Example I.

EXAMPLE XXXIII

The peptide [Ser$^{18}$, Phe$^{27}$]-pNPY(17–36) having the formula (SEQ ID NO:11): Leu-Ser-Arg-Tyr-Tyr-Ser-Ala-Leu-Arg-His-Phe-Ile-Asn-Leu-Ile-Thr-Arg-Gln-Arg-Tyr, wherein the C-terminus is amidated, is synthesized using the method as described in Example I.

EXAMPLE XXXIV

The peptide [N$^\alpha$MeIle$^{18}$,Gln$^{25}$, Phe$^{27}$]-Npy(18–36) is synthesized using the general method as described in Example I.

EXAMPLE XXXV

The peptide [D-Ser$^{18}$, Phe$^{36}$]-Npy(18–36) having the formula: H-D-Ser-Arg-Tyr-Tyr-Ser-Ala-Leu-Arg-His-Tyr-Ile-Asn-Leu-Ile-Thr-Arg-Gln-Arg-Phe-NH$_2$ is synthesized using the method as described in Example I.

EXAMPLE XXXVI

The peptide [Asp$^{23}$, Arg$^{26}$]-hNPy(17–36) having the formula (SEQ ID NO:12): Met-Ala-Arg-Tyr-Tyr-Ser-Asp-Leu-Arg-Arg-Tyr-Ile-Asn-Leu-Ile-Thr-Arg-Gln-Arg-Tyr, wherein the C-terminus is amidated, is synthesized using the method as described in Example I.

EXAMPLE XXXVII

The peptide [Glu$^{23}$, Ile$_{29}$]-NPY(18–36) having the formula (SEQ ID NO:13): Ala-Arg-Tyr-Tyr-Ser-Glu-Leu-Arg-His-Tyr-Ile-Ile-Leu-Ile-Thr-Arg-Gln-Arg-Tyr, wherein the C-terminus is amidated, is synthesized using the method as described in Example I.

EXAMPLE XXXVIII

The peptide [D-Ala$^{17}$]-NPY(17–36)-OH having the formula: D-Ala-Ala-Arg-Tyr-Tyr-Ser-Ala-Leu-Arg-His-Tyr-Ile-Asn-Leu-Ile-Thr-Arg-Gln-Arg-Tyr-OH is synthesized on a chloromethylated resin using the general method as described in Chemistry Letters, K. Horiki et al., 165–168 (1978).

EXAMPLE XXXIX

The peptide pPYY(17–36) is synthesized using the method as described in Example I.

EXAMPLE XL

The peptide pPYY(19–36) is synthesized using the method as described in Example I.

EXAMPLE XLI

The peptide pPYY(20–36) is synthesized using the method as described in Example I.

EXAMPLE XLII

The peptide pPYY(21–36) is synthesized using the method as described in Example I.

EXAMPLE XLIII

The peptides listed below are synthesized using the method of Example I.

| Peptide | $[\alpha]_D$ |
| --- | --- |
| [D-Tyr$^{21}$]-NPY(18–36) | −48.0° |
| [D-Ser$^{22}$]-NPY(18–36) | −36.0° |
| [D-Ala$^{23}$]-NPY(18–36) | −48.0° |
| [D-His$^{26}$]-NPY(18–36) | −38.0° |
| [D-Tyr$^{27}$]-NPY(18–36) | −40.0° |
| [D-Ile$^{28}$]-NPY(18–36) | −43.0° |
| [D-Asn$^{29}$]-NPY(18–36) | −38.0° |
| [D-Leu$^{30}$]-NPY(18–36) | −35.0° |
| [D-Ile$^{31}$]-NPY(18–36) | −38.0° |
| [D-Thr$^{32}$]-NPY(18–36) | −35.0° |
| [D-Arg$^{33}$]-NPY(18–36) | −39.4° |
| [D-Gln$^{34}$]-NPY(18–36) | −40.3° |
| [D-Arg$^{35}$]-NPY(18–36) | −41.0° |
| [D-Tyr$^{36}$]-NPY(18–36) | −48.9° |

These peptides are judged to be substantially pure using the TLC and HPLC. The optical rotations $[\alpha]_D$ of these peptides are measured in 1.0 M acetic acid (c=0.5) at about 25° C. and are reported above.

Synthetic NPY analogs are tested for their effect on mean arterial blood pressure (MAP) in conscious rats. Saline solutions of the peptides are injected intra-arterially into conscious rats, and arterial pressure is monitored via an indwelling femoral cannula directly coupled to a pressure transducer. MAP is calculated as [(systolic-diastolic/3)+diastolic] and is generally determined 1 minute after administration of the peptide and then at varying periods thereafter. Control animals receive saline vehicle alone.

pNPY(17-36), NPY(18-36) and NPY(19-36) significantly decrease MAP at five and ten minutes after administration. The maximal response is seen with NPY(1-8-36), which produces a fall in MAP from 102±2 mmHg to 50±6 mmHg after five minutes. All fragments increase heart rate (HR) after injection when compared to the control group. There is no significant difference in the maximal HR obtained between any of the fragments. PYY(17-36), PYY(19-36), PYY(20-36) and PYY(21-36) also significantly decrease MAP at 5 and 15 minute intervals. Because of the homology between the NPY and PYY, these fragments of PYY are broadly considered as NPY analogs.

NPY(18-36) decreases MAP in a dose-dependent manner. At five minutes after injection, there is no significant change in MAP in the group that received 10 µg, however, there is a significant decrease in MAP in the 30 µg group and a more pronounced effect in the groups that receive 100 and 300 µg. There is no significant difference in the decrease in MAP obtained after administration of 100 or 300 µg. All doses produce maximal decrease in MAP five minutes after administration, except for the 10 µg dose which has a nadir MAP at t=15 min. Heart rates are only significantly increased in the 30 µg group.

NPY is given to a group of animals that are pretreated with NPY(18-36) to determine if the hypotension seen after NPY(18-36) administration is due to antagonism of the hypertensive actions of NPY. The increase in MAP (a MAP) obtained by NPY administration (1 µg, intra-arterially) to animals pretreated with NPY(18-36) (300 µg) is not significantly different from that obtained after NPY administration to control animals (28±5 mmHg vs 32±5 mmHg, respectively, with 3 animals for each test).

The peptides disclosed in Example XLIII in which singular D-isomer substitutions were made in a C-terminal fragment of the NPY peptide, namely NPY(18-36), along with certain other NPY peptide analogs were tested for their effect on mean-arterial blood pressure (MAP) using the protocol set forth above. Saline solutions of the peptides were administered intraarterially in a 100-µL bolus in an amount equal to about 0.4 mg/Kg body weight. The change in MAP was measured by measuring the pressure just prior to administration and at intervals of minute for the first 5 minutes after administration, and then at intervals of 5 minutes each for 1 hour; the results set forth hereinafter were calculated as an average using the data obtained during the first 10 minutes following administration (with the indicated standard deviation of error based upon the variance in the number of animals actually treated, which in most cases was 6 rats). The results for these tests are set forth in Table 1 which follows:

TABLE 1

| Peptide | Δ MAP (mmHg) |
|---|---|
| [D-Tyr$^{20}$]-NPY(18-36) | −4.4 ± 7 |
| [D-Tyr$^{21}$]-NPY(18-36) | −53 ± 9 |
| [D-Ser$^{22}$]-NPY(18-36) | −37 ± 8 |
| [D-Ala$^{23}$]-NPY(18-36) | −25 ± 9 |
| [D-Leu$^{24}$]-NPY(18-36) | 0.1 ± 2 |
| [D-Arg$^{25}$]-NPY(18-36) | 6 ± 7 |
| [D-His$^{26}$]-NPY(18-36) | −13 ± 7 |
| [D-Tyr$^{27}$]-NPY(18-36) | −38 ± 10 |
| [D-Ile$^{28}$]-NPY(18-36) | −14 ± 10 |
| [D-Asn$^{29}$]-NPY(18-36) | −30 ± 15 |
| [D-Leu$^{30}$]-NPY(18-36) | −40 ± 6 |
| [D-Ile$^{31}$]-NPY(18-36) | −41 ± 5 |
| [D-Thr$^{32}$]-NPY(18-36) | −32 ± 9 |
| [D-Arg$^{33}$]-NPY(18-36) | −25 ± 8 |
| [D-Gln$^{34}$]-NPY(18-36) | −32 ± 11 |
| [D-Arg$^{35}$]-NPY(18-36) | −45 ± 12 |
| [D-Tyr$^{36}$]-NPY(18-36) | −36 ± 10 | pNPY also transiently elevates intracellular Ca++ concentrations with an EC$_{50}$ of 2.0 nM. Maximal Ca++ increases are 200-550 nM above basal levels (40-70 nM). NPY(18-36) (100 nM) increases Ca++ less than 10% as much as does an equal concentration of NPY, indicating that NPY(18-36) is only a very weak agonist in this system. Moreover, NPY(18-36) does not antagonize the Ca++ mobilization by NPY; after addition of 100 nM NPY (18-36), 100 nM NPY still elevates intracellular Ca++ to the same extent as under control conditions. Furthermore, pNPY(18-36) neither inhibits cAMP formation nor antagonizes NPY-mediated inhibition.

NPY analogs or nontoxic addition salts thereof, combined with a pharmaceutically acceptable carrier to form a pharmaceutical composition, may be administered to mammals, including humans, either intravenously, subcutaneously, intramuscularly, percutaneously, e.g.intranasally, intracerebrospinally, orally or by suppository. The peptide should be at least about 90% pure and preferably should have a purity of at least about 98% when administered to humans. This purity means that the intended peptide constitutes the stated weight % of all like peptides and peptide fragments present. Administration may be employed by a physician to lower blood pressure to counteract hypertension; the required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 1 to about 200 micrograms of the peptide per kilogram of the body weight of the host. As used herein all temperatures are ° C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, fragments of PYY that are further N-terminally shortened by one or several residues, e.g. PYY(22-36) are also expected to have a similar effect upon MAP. In many instances the C-terminal free acid has substantially the same biological effect as the C-terminal amide, and thus they are considered to be equivalents.

Various features of the invention are emphasized in the claims which follow.

---

What is claimed is:

1. A method for lowering the blood pressure of a mammal, which method comprises administering to said mammal an effective amount of a peptide or a nontoxic salt thereof, having one of the following formulae:

(a) H-ala-Arg-Tyr-$Xaa_{21}$-$Xaa_{22}$-Ala-Leu-Arg-His-$Xaa_{27}$-Ile-$Xaa_{29}$-$Xaa_{30}$-$Xaa_{31}$-$Xaa_{32}$-Arg-$Xaa_{34}$-$Xaa_{35}$-$Xaa_{36}$-$NH_2$ wherein $Xaa_{21}$ is Tyr or D-Tyr; $Xaa_{22}$ is Ser or D-Ser; $Xaa_{27}$ is Tyr or D-Tyr; $Xaa_{29}$ is Asn or D-Asn; $Xaa_{30}$ is Leu or D-Leu; $Xaa_{31}$ is Ile or D-Ile; $Xaa_{32}$ is Thr or D-Thr; $Xaa_{34}$ is Gln or D-Gln; $Xaa_{35}$ is Arg or D-Arg; and $Xaa_{36}$ is Tyr or D-Tyr; and wherein one D-isomer is present from among $Xaa_{21}$, $Xaa_{22}$, $Xaa_{27}$, $Xaa_{29}$, $Xaa_{30}$, $Xaa_{31}$, $Xaa_{32}$, $Xaa_{34}$, $Xaa_{35}$ and $Xaa_{36}$; or (b) H-Ser-Arg-Tyr-$Xaa_{21}$-$Xaa_{22}$-Ser-Leu-Arg-His-$Xaa_{27}$-Leu-$Xaa_{29}$-$Xaa_{30}$-$Xaa_{31}$-$Xaa_{32}$-Arg-$Xaa_{34}$-$Xaa_{35}$-$Xaa_{36}$-$NH_2$, wherein $Xaa_{21}$ is Tyr or D-Tyr; $Xaa_{22}$ is Ala or D-Ala; $Xaa_{27}$ is Tyr or D-Tyr; $Xaa_{29}$ is Asn or D-Asn; $Xaa_{30}$ is Leu or D-Leu; $Xaa_{31}$ is Val or D-Val; $Xaa_{32}$ is Thr or D-Thr; $Xaa_{34}$ is Gln or D-Gln; $Xaa_{35}$ is Arg or D-Arg; and $Xaa_{36}$ is Tyr or D-Tyr; and wherein one D-isomer is present from among $Xaa_{21}$, $Xaa_{22}$, $Xaa_{27}$, $Xaa_{29}$, $Xaa_{30}$, $Xaa_{31}$, $Xaa_{32}$, $Xaa_{34}$, $Xaa_{35}$ and $Xaa_{36}$.

2. The method of claim 1 wherein $Xaa_{21}$ is D-Tyr.

3. The method of claim 1 wherein the peptide has formula (a) and $Xaa_{31}$ is D-Ile.

4. The method of claim 1 wherein $Xaa_{35}$ is D-Arg.

5. The method of claim 1 wherein $Xaa_{36}$ is D-Tyr.

6. A peptide having the formula: H-Ala-Arg-Tyr-$Xaa_{21}$-$Xaa_{22}$-Ala-Leu-Arg-His-$Xaa_{27}$-Ile-$Xaa_{29}$-$Xaa_{30}$-$Xaa_{31}$-$Xaa_{32}$-Arg-$Xaa_{34}$-$Xaa_{35}$-$Xaa_{36}$-$NH_2$, wherein $Xaa_{21}$ is Tyr or D-Tyr, $Xaa_{22}$ is Ser or D-Ser, $Xaa_{27}$ is Tyr or D-Tyr, $Xaa_{29}$ is Asn or D-Asn, $Xaa_{30}$ is Leu or D-leu, $Xaa_{31}$ is Ile or D-Ile, $Xaa_{232}$ is Thr or D-Thr, $Xaa_{34}$ is Gln or D-Gln, $Xaa_{35}$ is Arg or D-Aeg, and $Xaa_{36}$ is Tyr or D-Tyr; provided that one D-isomer is present from among $Xaa_{21}$, $Xaa_{22}$, $Xaa_{27}$, $Xaa_{29}$, $Xaa_{30}$, $Xaa_{31}$, $Xaa_{32}$, $Xaa_{34}$, $Xaa_{35}$ and $Xaa_{36}$.

7. A peptide according to claim 6 wherein the peptide is selected from the group consisting of -NPY (18-36), -NPY (18-36), -NPY (1-8-36), -NPY (18-36), -NPY (18-36) and -NPY (18-36).

8. A peptide according to claim 6 wherein $Xaa_{21}$ is D-Tyr.

9. A peptide according to claim 6 wherein $Xaa_{35}$ is D-Arg.

10. A peptide according to claim 6 wherein $Xaa_{30}$ is D-Leu.

11. A peptide according to claim 6 wherein $Xaa_{30}$ is D-Ile.

12. A pharmaceutical composition for lowering blood pressure comprising an effective amount of a peptide as set forth in claim 7 and a pharmaceutically acceptable liquid or solid carrier therefor.

13. A peptide having the formula: H-$Xaa_{18}$-Arg-Tyr-$Xaa_{21}$-$Xaa_{22}$-$Xaa_{23}$-Leu-Arg-His-$Xaa_{27}$-$Xaa_{28}$-$Xaa_{29}$-$Xaa_{30}$-$Xaa_{31}$-$Xaa_{32}$-Arg-$Xaa_{34}$-$Xaa_{35}$-$Xaa_{36}$-$NH_2$,
wherein $Xaa_{18}$ is Ala or Ser; $Xaa_{21}$ is Tyr or D-Tyr; $Xaa_{22}$ is Ser, D-Ser, Ala or D-Ala; $Xaa_{23}$ is Ala or Ser; $Xaa_{27}$ is Tyr or D-Tyr; $Xaa_{28}$ is Ile or Leu; $Xaa_{29}$ is Asn or D-Asn; $Xaa_{30}$ is Leu or D-Leu; $Xaa_{31}$ is Ile, D-Ile, Val or D-Val; $Xaa_{32}$ is Thr or D-Thr; $Xaa_{34}$ is Gln or D-Gln; $Xaa_{35}$ is Arg or D-Arg; and $Xaa_{36}$ is Tyr or D-Tyr; provided that one D-isomer is present from among $Xaa_{21}$, $Xaa_{22}$, $Xaa_{27}$, $Xaa_{29}$, $Xaa_{30}$, $Xaa_{31}$, $Xaa_{32}$, $Xaa_{34}$, $Xaa_{35}$ and $Xaa_{36}$.

14. A peptide according to claim 13 wherein the peptide has the formula: H-Ser-Arg-Tyr-$Xaa_{21}$-$Xaa_{22}$-Ser-Leu-Arg-His-$Xaa_{27}$-Leu-$Xaa_{29}$-$Xaa_{30}$-$Xaa_{31}$-$Xaa_{32}$-Arg-$Xaa_{34}$-$Xaa_{35}$-$Xaa_{36}$-$NH_2$.

15. A peptide according to claim 14 wherein $Xaa_{21}$ is D-Tyr.

16. A peptide according to claim 14 wherein $Xaa_{35}$ is D-Arg.

17. A peptide according to claim 13 in the form of -NPY(18-36).

18. A peptide according to claim 13 in the form of -NPY(18-36).

19. A method according to claim 1 wherein an effective amount of -NPY(18-36) in a pharmaceutically acceptable carrier is administered intravenously.

* * * * *

UNITED STATES PATENT AND TRADEMARK OFFICE
CERTIFICATE OF CORRECTION

PATENT NO. : 5,328,899
DATED : July 12, 1994
INVENTOR(S) : Boublik et al.

It is certified that error appears in the above-indentified patent and that said Letters Patent is hereby corrected as shown below:

Column 21, Claim 1, line 31, change "H-ala-" to -- H-Ala- --; Column 21, Claim 6, line 61, change "D-leu" to -- D-Leu --; same line, change "$Xaa_{232}$" to -- $Xaa_{32}$ --; line 62, change "D-Aeg" to -- D-Arg --; Column 21, Claim 7, line 67, after "of", insert -- [$D-Tyr^{21}$] --; Column 22, Claim 7, change lines 27 and 28 to read: -- [$D-Ser^{22}$]-NPY(18-36), [$D-Ile^{31}$]-NPY(18-36), [$D-Thr^{32}$]-NPY(18-36), [$D-Arg^{35}$]-NPY(18-36) and [$D-Tyr^{36}$]-NPY(18-36). --; Column 22, Claim 11, line 35, change "$Xaa_{30}$" to -- $Xaa_{31}$ --; Column 22, Claim 17, line 61, after "of", insert -- [$D-Tyr^{21}$] --; Column 22, Claim 18, line 63, after "of", insert -- [$D-Arg^{35}$] --; Column 22, Claim 19, line 66, after "of", insert -- [$D-Tyr^{21}$] --.

Signed and Sealed this

Twenty-fifth Day of October, 1994

Attest:

Attesting Officer

BRUCE LEHMAN

Commissioner of Patents and Trademarks